United States Patent [19]

Marcune

[11] Patent Number: 4,741,329
[45] Date of Patent: May 3, 1988

[54] SURGICAL APPLIANCE FOR STIMULATING AN ERECTION

[75] Inventor: Benjamin F. Marcune, Rydal, Pa.

[73] Assignee: Lehigh Group Ltd, West Chester, Pa.

[21] Appl. No.: 862,987

[22] Filed: May 14, 1986

[51] Int. Cl.⁴ .............................................. A61F 5/41
[52] U.S. Cl. ..................................................... 128/79
[58] Field of Search .......................................... 128/79

[56] References Cited

U.S. PATENT DOCUMENTS

| | | | |
|---|---|---|---|
| 1,225,341 | 5/1917 | Lederer | 128/79 |
| 2,874,698 | 2/1959 | Sell | 128/79 |
| 3,421,504 | 1/1969 | Gibbons | 128/79 |
| 3,631,853 | 1/1972 | Burdette, Jr. | 128/79 |
| 3,744,486 | 7/1973 | Wilson | 128/79 |
| 4,203,432 | 5/1980 | Koch | 128/79 |

FOREIGN PATENT DOCUMENTS 2129688 5/1984 United Kingdom ................ 128/79

Primary Examiner—Robert P. Swiatek
Assistant Examiner—Cary E. Stone
Attorney, Agent, or Firm—Ratner & Prestia

[57] ABSTRACT

The present invention teaches a surgical appliance for stimulating an erection of the male genital organ by creating a high vacuum around the male genital organ. The surgical appliance includes a vacuum housing for receiving the male penis therein and is provided with a seal at the base thereof. A pump housing is connected to the vacuum housing and is provided with a high vacuum pump therein. An activating lever is provided along one side of the housing to enable the appliance to be operated with one hand. In the preferred mode of operation, a constriction ring is cooperable with the surgical appliance to maintain an erection after it is achieved.

17 Claims, 5 Drawing Sheets

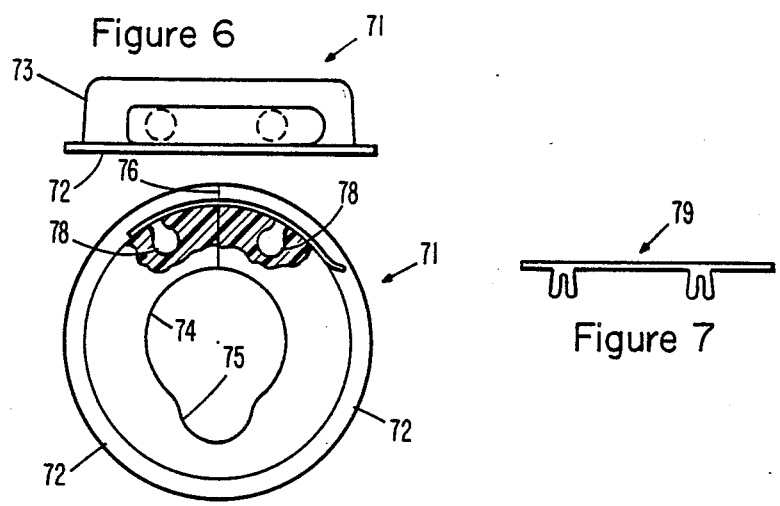
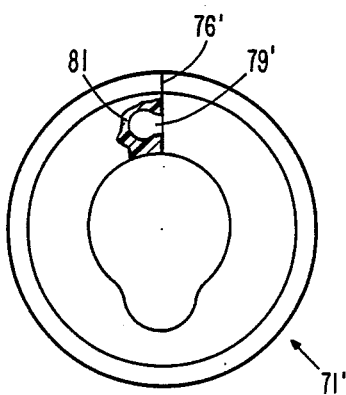

SURGICAL APPLIANCE FOR STIMULATING AN ERECTION

BACKGROUND OF THE INVENTION

1. Field of the Invention

The present invention relates to a surgical appliance adapted to stimulate an erection of the male genital organ. More particularly, the invention relates to a high vacuum apparatus which induces flow of blood into the corpora cavernosa tissues as well as the corpus spongiosum tissues.

2. Description of the Prior Art

Surgical devices are classified in U.S. Class 128. Suction devices are classified in subclasses 300, 303, etc. and orthopedic appliances are classified in subclass 79.

The inability to attain and maintain an erection of the male genital organ has long been recognized as a problem with some males. While the problem is more common to men of advanced age, it is also becoming increasingly common among younger men, particularly those subject to psychological stress and/or poor blood circulation. Surgical penile implants have met with a high degree of success in stimulating an erection, but do not necessarily create an enlargement of the aforementioned penile erectile tissues with blood.

The male penis consists mainly of three spongy erectile tissues, two large corpora cavernosa tissues and a smaller corpus spongiosum tissue which insheaths the urethra. Erection of the penis occurs when the spongy erectile tissues are rapidly filled with blood which compresses the veins which ordinarily drain the penis. Blood is retained in the tissues that would normally be drained from the penis causing stiffness or an erection.

Normally, an erection of the penis results from an increased blood flow in the dorsal and profunda arteries flowing into the large corpora cavernosa tissues and an increased blood flow in the bulbo-urethral arteries flowing into the smaller corpus spongiosum tissue. Vasodilation of the arteries feeding the erectile tissues may be effected by the central nervous system exciting or activating the neuro vascular bundle of nerves located near the prostate gland behind the scrotum. Local stimulation of the nervous fibers in the penis may also induce vasodilation of the arteries supplying the erectile tissues of the penis. If the arteries are not adaquately vasodilated and/or if the erectile tissue is not adaquately compressed to constrict the flow of blood from the erectile tissues in the veins, then external means of effecting an erection becomes necessary. The aforementioned surgical implants do not of themselves enhance vasodilation of the arteries.

Apparatus employing hypodermic needles for injecting vasodilatory fluids into the corpora cavernosa to dilate the profunda and the dorsal arteries are not desirable because the needles break the skin of the penis exposing the user to harmful or even fatal diseases. Such devices require a high degree of skill to effect proper injections and also inflict both pain and psychological shock in the process.

Apparatus for applying a suction or partial vacuum to the male penis are known. Numerous such devices are found in U.S. art class 128, subclasses 79 and 303. Suction apparatus, if operated properly, produces a partial vacuum surrounding the penis which induces blood flow into the erectile tissues. Some prior art suction devices are also provided with elastic bands which may be transferred from the end of the suction device when some degree of erection is achieved. The elastic band is preferably transferred to the base of the penis to retard blood flow from the erectile tissues, thus, maintaining an erection for a longer time.

Vibrators, devices which cause compression and/or create suction are employed as stimulators to induce blood flow into the erectile tissues. Elastic bands, tourniquets, straps and elastic sleeves have also been employed to impede blood flow from the penis once erection is achieved. Some of these latter devices are known to cut off the blood flow from and/or to the penis and can result in damage to nerves and/or tissue.

It would be desirable to provide a surgical appliance which is adapted to be operated with one hand and which accomplishes the desired inducement of blood flow into the erectile tissure of the penis. The desirable apparatus would be continuously adjustable to adapt to different users who need either a high or a low level of stimulation and/or induced blood flow into the erectile tissues.

SUMMARY OF THE INVENTION

It is a principal object of the present invention to provide a unitary portable surgical appliance for inducing an erection of the male penis.

It is another object of the present invention to provide a surgical appliance which is operable with only one hand for inducing a partial vacuum around the male penis.

It is another object of the present invention to provide a unitary surgical appliance having a lever-operated vacuum pump that is simple to control.

It is another object of the present invention to provide an adjustable, hand operated, high vacuum pump in a unitary surgical appliance.

It is another object of the present invention to provide a hand-operated vacuum pump which creates a pulsating vibratory motion during normal operation.

It is yet another object of the present invention to provide a surgical appliance with a novel durable vacuum seal.

It is yet another object of the present invention to provide a novel constricting ring which is cooperable with the vacuum seal on the surgical appliance and is adapted to be custom fitted or sized to a male penis.

It is yet another object of the present invention to provide a novel constricting ring which has a quick release feature.

It is a general object of the present invention to provide a surgical appliance which is capable of producing an adjustable vacuum which is sufficiently high to induce an erection in impotent males with psychogenic or physical dysfunction.

It is another general object of the present invention to provide a surgical appliance for inducing blood flow into the erectile tissue of the male penis to exercise the penile tissue and to provide a lengthening and enlargement of the expanded penis in the flacid state as well as to enlarge the penis size over the normal erect state.

According to these and other objects of the present invention, there is provided an elongated surgical appliance having a vacuum housing at one end for loosely receiving therein the male penis, a vacuum pump having a vacuum plenum is connected to the other end of the vacuum housing for providing a high vacuum in the vacuum plenum and vacuum chamber, a pump lever extends along the side wall of the vacuum housing and is connected to the vacuum pump so that it is operable with the same hand which supports the vacuum chamber, each successive operation of the pump lever produces an increasingly higher vacuum in the vacuum chamber to effect blood flow in the erectile tissue and to effect erection of the male penis.

BRIEF DESCRIPTION OF THE DRAWINGS

FIG. 5 is a front view of the detachable constricting ring;

FIG. 6 is a top view of the detachable ring shown in FIG. 5;

FIG. 7 is a side view of the lock shown in FIG. 6;

FIG. 8 is a front view of a modified detachable ring of the type shown in FIG. 5;

DESCRIPTION OF THE PREFERRED EMBODIMENT

Figure 1:
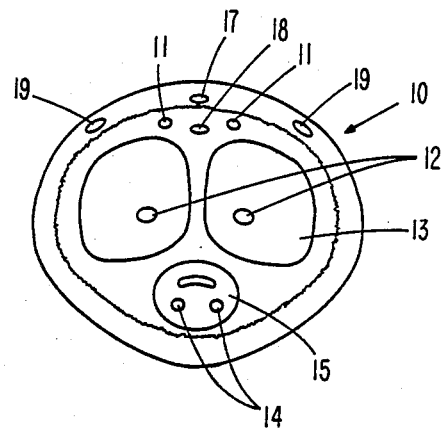
FIG. 1 is a diagramatic section taken through the male penis.

Refer now to FIG. 1 showing a cross-section view through a male penis 10. The inability of the penis to achieve an erection may be psychological or physiological in nature, however, the immediate cause for the failure to produce an adaquate erection results from incomplete inflation of the corpora cavernosa erectile tissue 13 with blood. Normally under nervous stimulation the dorsal arteries 11 and the profunda (or deep penile) arteries 12 will be dialated to increase blood flow to the corpora cavernosa tissue 13. The rapid filling of the spongy erectile tissues with blood compresses the veins in the tissues which would ordinarily drain the tissues, thus, resulting in stiffness or erection of the penis. The bulbo-urethral artery 14, when dilated, fills the spongy erectile tissues of the corpus spongiosum tissue 15 surrounding the urethra and further enhances stiffness or erection of the penis.

Superficial dorsal veins 17 and lateral veins 19, as well as deep dorsal vein 18 drains the blood from the erectile tissues. If the flow of the blood is restricted or impeded in the veins, the erection can be prolonged or maintained over a relatively long period.

Figure 2:
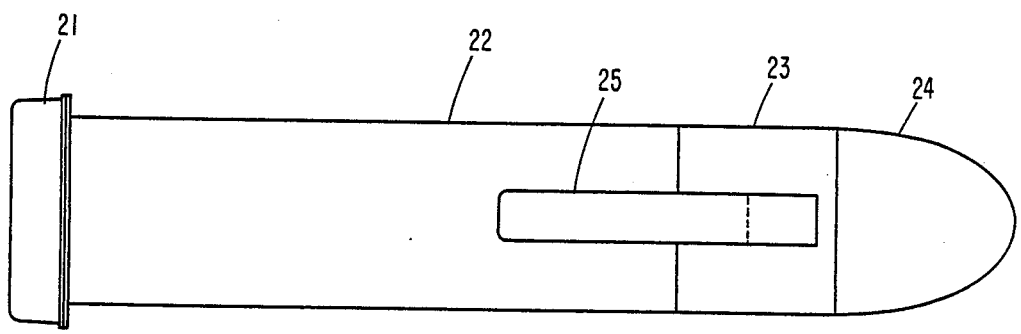
FIG. 2 is a top or plan view of a preferred embodiment surgical apparatus.
Figure 3:
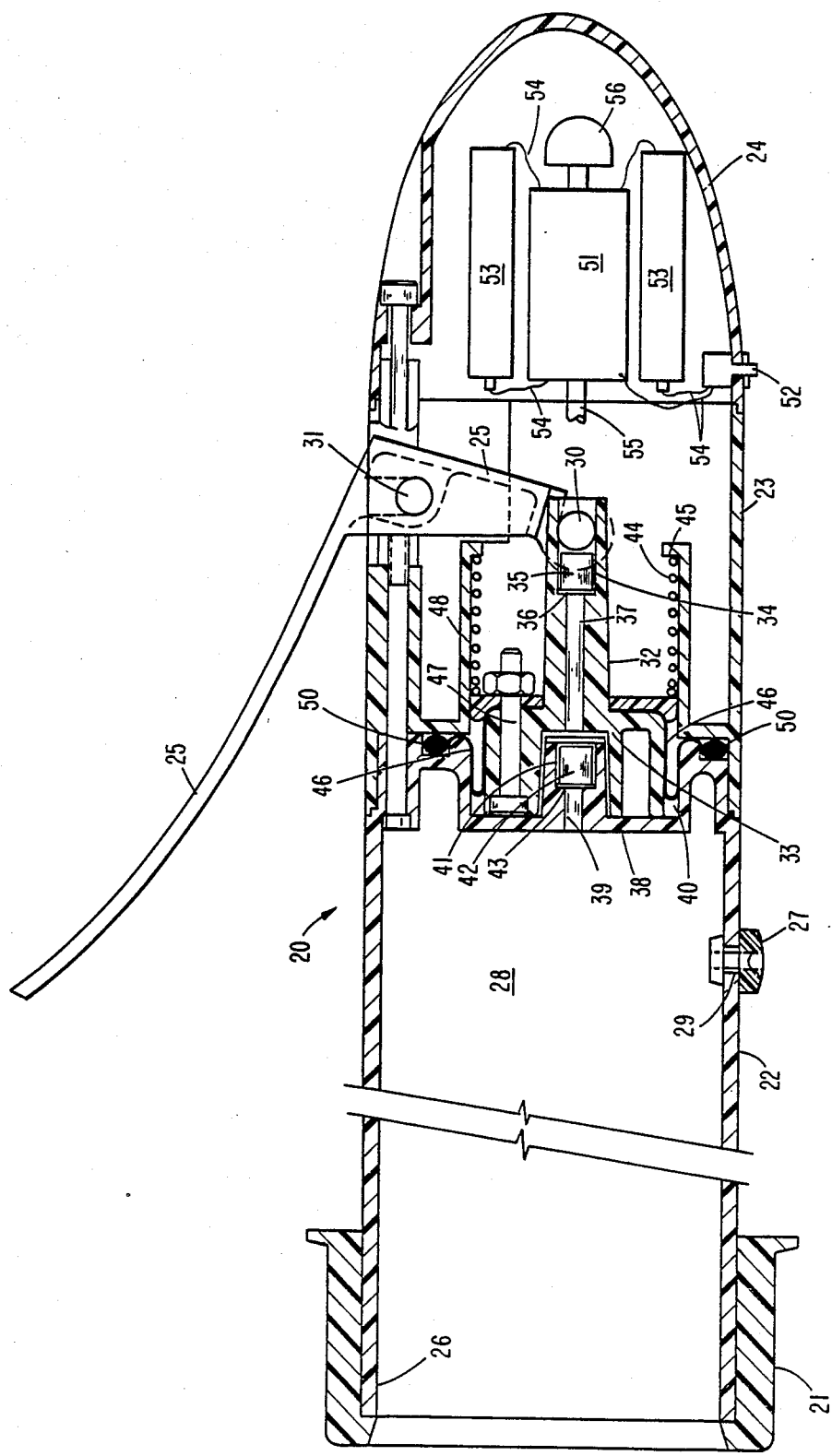
FIG. 3 is an enlarged side view in partial section of the apparatus shown in FIG. 2.

Refer now to FIGS. 2 and 3 showing a top and side view of a preferred embodiment appliance 20 for stimulating an erection of the male penis. The appliance 20 comprises a soft seal 21 on the open end of the main vacuum housing 22. Preferably, housing 22 is a rigid clear plastic. A pump housing 23 is connected to the closed end of housing 22. A nose cone housing 24 is connected to housing 22 and provides a cover for a vibrator or electric pump drive as will be explained hereinafter. The preferred mode of operation of the vacuum pump in housing 23 is by manual operation of lever 25 with the thumb or fingers while holding and operating the appliance 20 with one hand. The pump is designed to impart a vibratory motion to the penis which further enhances and stimulates the nerves.

Refer now to FIG. 3 showing in elevation the details of a BELLOFRAM pump in enlarged partial section. Soft plastic seal 21 is permanently attached to the open end 26 of housing 22 and is adapted to serve as a vacuum seal against the body at the base of the penis in one mode of operation. A resilient relief valve 27 is mounted through a hole 29 in the side of housing 22 and is operable to allow air to enter the vacuum chamber 28 of housing 22 when distorted laterally to uncover a portion of hole 29.

Lever 25 is pivotally mounted on a pivot pin 31 in pump housing 23. The short end of lever 25 is pivotally mounted to a piston rod 32 of piston 33 by pin 30. Piston rod 32 has a cylindrical recess 34 in which a check valve plug 35 is free to move. A resilient disk seal 36 is cooperable with plug 35 and is adapted to seal conduit 37 during a suction stroke of piston 33.

The end wall 38 of housing 22 forms a wall of a plenum chamber 40. Wall 38 is provided with an aperture or conduit 39 which opens into a cylindrical recess 41 in which a check valve plug 42 is free to move. A resilient seal 43 cooperates with plug 42 and is adapted to seal conduit 39 during a return stroke of piston 33. When lever 25 is depressed, valve 35, 36 seals conduit 37 and starts creating a partial vacuum in plenum 40. When the pressure in plennum 40 falls below the pressure in chamber 28, valve 42, 43 opens and the pressure in chamber 28 if further reduced. As lever 25 is released, compression spring 44 acting on clamp disk 45 returns piston 33 to the position shown.

BELLOFRAM disk 46 is shown folded in plenum 40. During the suction stroke, the flexible disk 45 unfolds as piston 33 moves to the right. BELLOFRAM disk 46 forms a moveable wall of the plenum 40 similar to a bellows. Cap screws 47 in piston 33 hold the inner diameter of disk 46 sealed against piston 33. Spring cage 48 of pump housing 23 holds the outer diameter of BELLOFRAM disk 46 sealed against end wall 38 of vacuum housing 22. Tie rods 49 hold the vacuum housing 22, the pump housing 23 and cone housing 24 tightly together and also compresses the end ring 50 of BELLOFRAM disk 46 against end wall 38.

A desirable feature of the BELLOFRAM disk 46 is that it permits piston pin 30 to be moved through an arcuate path which tilts piston 33. Clamp disk 45 is loosely fitted in spring case 48 which serves as a guide for movement of piston 33. BELLOFRAM disk 46 does not rub against either piston 33 or end wall 38, thus, is not subject to friction wear which could cause loss of the high vacuum seal achieved in the preferred embodiment of the present invention. The structure shown has been tested and is capable of achieving vacuum pressures in excess of twenty-two inches of mercury, which is double the best vacuum pressure achieved with a normal piston employing a moving friction seal against a cylindrical sidewall. Depression of lever 25 starts the suction stroke that eventually creates a vacuum in plenum 40 high enough so that the vacuum in chamber 28 causes valve 42, 43 to rapidly open. This rapid opening results in a pulsating and stimulating action which enhances dilation of the arteries.

When additional stimulation is desired, a vibrating solenoid 51, shown schematically, may be mounted in the nose cone 24. Push button switch 52 is electrically connected to the solenoid 51 and batteries 53 by wires 54 to control operation of the solenoid. It will be understood that solenoid 53 is axially aligned with piston rod 32 and may be connected thereto by a shaft or rod 55.

When solenoid 51 is also employed to drive piston 33, bumper stop 56 is preferably connected on shaft 55 to limit the travel of the shaft 55, and lever 25 is disconnected from piston rod 32. The electric pump feature need not be employed when the patient-user has sufficient manual dexterity to actuate and control lever 25.

Figure 4:
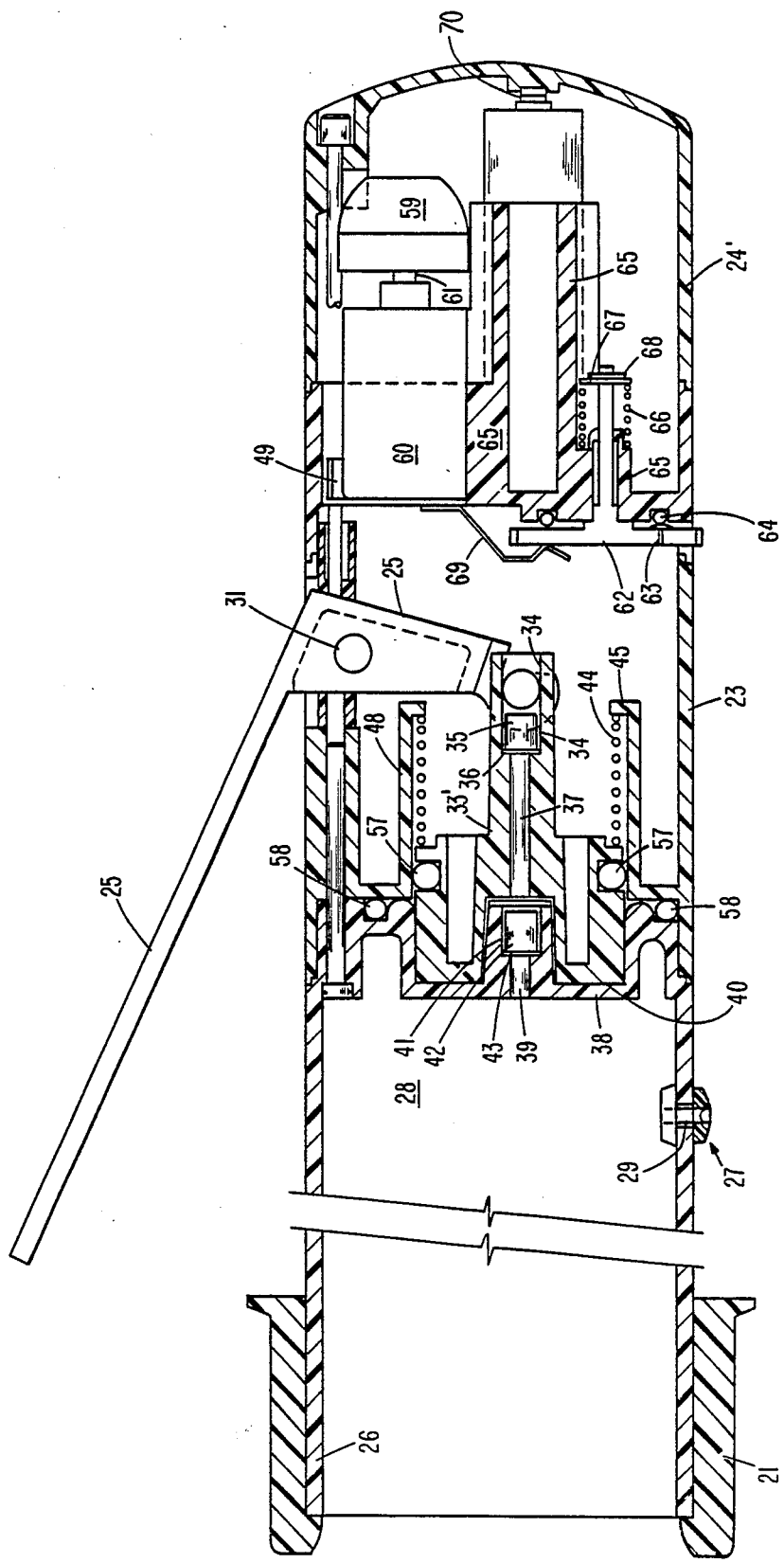
FIG. 4 is an enlarged side view in partial section of a modified embodiment apparatus shown in FIG. 3.

Refer now to FIG. 4 showing in side elevation an enlarged partial section of a modified embodiment apparatus. The FIG. 4 embodiment has a modified piston 33' that employs a moving friction O-ring seal 57, and a fixed O-ring seal 58, otherwise the parts are the same as those shown in FIG. 3 and are numbered the same.

Nose cone 24' is larger than before and is shaped to receive a small efficient electric motor 60 having an eccentric weight 59 mounted on its rotating shaft 61. Adjustment wheel 62 is provided with a wheel contact 63 which engages reostat coil 64. Wheel 62 is mounted on the battery and motor support frame 65 and is biased into engagement with coil 64 by spring 66, held in compression by washer 67 and clip 68. Wheel contact 63 provides ON-OFF regulation as well as speed adjustment regulation of motor 60. Electrical contacts 69 and 70 are shown as connected to the battery and motor, however, the electrical wires which connect the reostat-switch with the motor and battery are well known and are not shown in this illustration.

It will be understood that motor 60 is speed adjustable by reostat 64 for changing the frequency of the vibratory motion generated by eccentric weight 59. The vibration motor 60 is more efficient than a solenoid 51 shown in FIG. 3. However, motor 60 must be modified if it is desired to drive the short end of lever 27 through a lever and link, not shown in this embodiment. Whenever the motor is modified to drive the piston 33' in a manner shown in FIG. 3, vibration is created as a result of the pumping action.

The hereinbefore described apparatus 20 has a soft end seal 21 which will enable the average user to make a seal against the body in the presence of pubic hair which is sufficient to create an average vacuum. With the aid of surgical jelly even a higher vacuum is achieved in chamber 22. Once an erection is achieved and the apparatus removed, the blood engorged in the erectile tissues may return by venal flow to the body unless the sphincter muscles restrict the return flow. It is known that constricting devices applied to the outside of the penis in the form of a tourniquet will assist in maintaining an erection by restricting the return venal blood flow but the arterial blood flow should be unrestricted. Since the arteries in the penis are more deeply embedded than the veins in the penis and are to some extent protected by the erectile tissues during an erection, devices which apply radially inward pressure to constrict venal blood flow have succeeded in assisting the sphincter muscles in maintaining an erection once achieved. However, it has been difficult to impossible to provide a proper degree of venal restriction. The amount of restriction desired varies from one person to another. Not only does the circumference and diameter of the penis vary considerably from one person to another, but the size will vary with the degree of erection that can be maintained without a constricting device. If too little constriction is applied, the constricting device will not maintain a prolonged erection. If too great a degree of restriction is applied, distractive discomfort, numbness and even damage to tissue may occur. The only practical solution to this problem is to provide a surgically designed and surgically fitted constrictive device.

Refer now to FIGS. 5 and 6 showing in front and top views, a novel constriction device. Ring 71 is adapted to be used with the preferred embodiment apparatus 20 shown in FIGS. 3 and 4. Unlike most prior art devices, the ring 71 does not of itself exert a radially inward pressure similar to an elastic band or elastic strap but is surgically designed and provided with an interior aperture 74 which is not constrictive when the penis is flacid. Moreover, the novel constriction ring 71 is adapted to be used with the apparatus 20 in one of two perferred modes of operation which will be explained in more detail hereinafter. Ring 71 has a radial flange 72 and an axial tapered portion 73 which permits the constriction ring to be mounted on the male penis before using the apparatus 20, or to be mounted in the apparatus 20 before the flacid penis is induced to full erection with apparatus 20. Once the penis reaches full erection, it enlarges when the arterial blood fills the erectile tissues. The enlarged penis presses radially outward on the aperture 74. The size and shape of the aperture 74 has been surgically determined to achieve and maintain full erection with the minimum constriction of blood flow in the penis. It has been found that use of the apparatus actually increases the diameter and the length of the penis of the average user, and more than one surgical constriction ring is desirable for the average user.

The interior aperture 74 is not round, but is relieved at portion 75 opposite the bulbo-urethral arteries 14 shown in FIG. 1. Ring 71 is flexible, but is sufficiently rigid to maintain its desired surgical shape shown without creating excessive pressure on the dorsal arteries 11 or the bulbo-urethral arteries 14. Ring 71 may be made in a single continuous molded piece, or provided with a break or split 76 which is preferred. The preferred embodiment quick release ring 71 shown in FIGS. 5 and 6 is provided with a snap-lock 79 shown in FIG. 7. The snap-lock 79 is adapted to snap into recesse 78 shown in ring 71.

FIG. 8 shows a modified quick release split lock constriction ring 71' having a lock 79' insert molded integrally with the ring and adapted to snap into recess 81. The lock 79' and recess 81 may take any of numerous forms such as a tapered wedge and keystone shapes all of which are adapted to provide a seal at the split 76' and permits the constriction ring 71' to be removed or installed by the user in a flacid or erect state.

Figure 9:
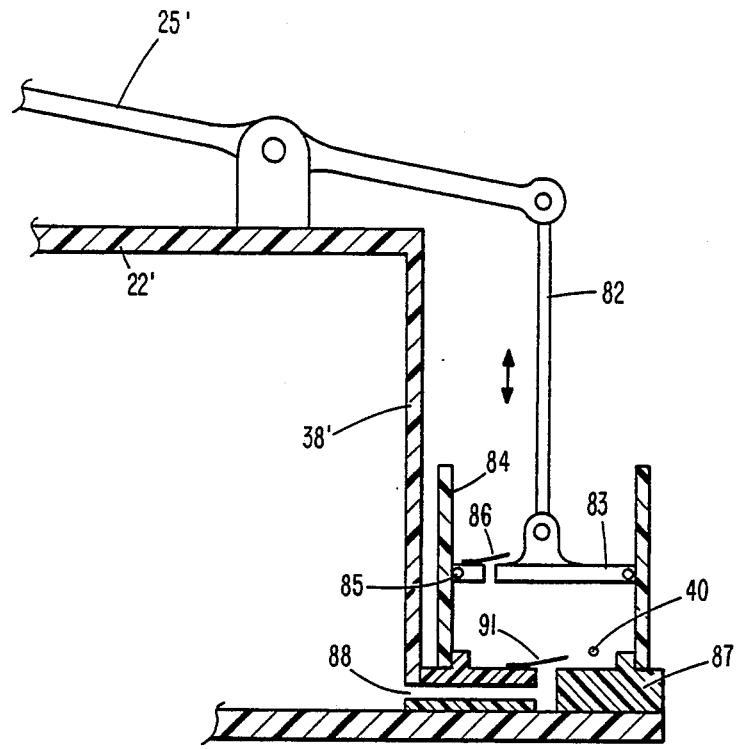
FIG. 9 is a schematic side view in enlarged section of another modified vacuum pump and plenum.

Refer now to FIG. 9 showing an enlarged schematic side view in section of a modified vacuum pump and plenum. Lever 25' is pivotally mounted on the outside of housing 22'. Pin connected lever 82 is connected to piston 83 and is movably mounted in cylinder 84. Piston 83 is provided with a seal 85 and a flap check valve 86. The base 87 is cross bored to provide a conduit 88 which connects plenum 40 with the vacuum chamber of housing 22'. Flap check valve 91 seals off conduit 88 during a return stroke. As discussed hereinbefore, the friction seal 85 tends to wear, leak, expand and stick unless special materials such as anti-friction plastics are employed. The advantage of such a device resides in the ease and cheapness of manufacture, thus, making the surgical appliance available to persons who could not ordinarily afford a more reliable and more expensive high vacuum device.

Figure 10:
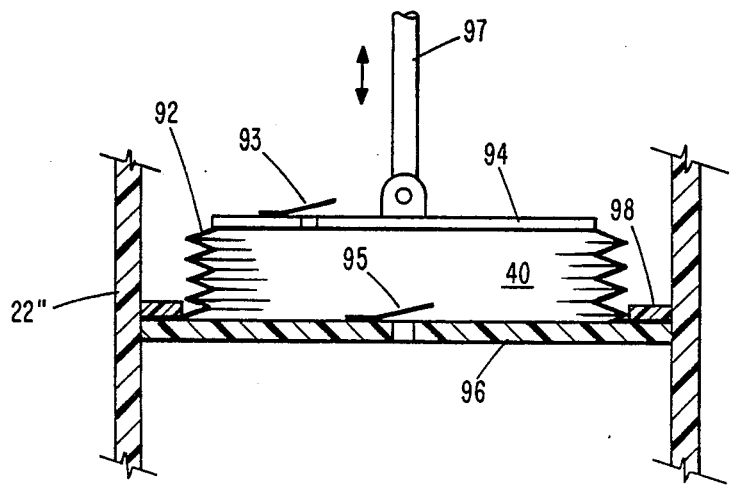
FIG. 10 is a schematic side view in enlarged section of yet another modified vacuum pump and plenum.

Refer now to FIG. 10 showing yet another enlarged schematic side view in section of a further modified vacuum pump and plenum. Plastic bellow 92 maybe molded of plastic to provide an easily constructed vacuum pump. Flap check valve 93 is mounted on rigid drive disk 94 and flap check valve 95 is mounted on end wall 96 of vacuum chamber 22". Lever 97 is driven by a force applied in alternate directions by means discussed hereinbefore. The retainer ring 98 is adapted to hold plastic bellows 92 against end wall 96.

It will be understood that FIGS. 9 and 10 are intended to illustrate a basic mode of operation and structure having a very small plenum chamber 40 combined with a tight seal which will enable the apparatus to achieve an average vacuum with a rubbing seal and a high vacuum with a preferred embodiment seal. When the plenum chamber is made very small, a high vacuum is achieved in the first part of the first suction stroke. Thus, each successive stroke creates a high vacuum in the plenum which is transferred to the vacuum chamber, rapidly reducing the pressure therein. When a high vacuum is applied around the total area of the male penis, vasodilation occurs immediately. When the penis fills the constriction ring 71 the compressed veins in the outer peripheral area of the penis are now contracted, thus, maintaining a full erection.

Having explained a preferred embodiment apparatus and three modifications thereof, it will be understood that the apparatus may be used in several desirable modes. The apparatus 20 and ring 71 may be assembled before use. When a full hard erection is achieved, the apparatus 20 may be separated from the ring 71 and the full erectile tissues will be expanded or exercised. Exercise of the erectile tissues with or without the constriction ring 71 will result in a semi-permenant enlargement of the penis over a short period of time, thus, resulting in a larger and more rigid normal erection.

The ring 71 may be placed on the penis before or after a full or partial erection is achieved. The erection may have been achieved with or without the use of the apparatus 20. Apparatus 20 may be subsequently employed at any time to achieve a full and hard erection. Thus, during prolonged foreplay it is possible to loose a full hard erection. The present apparatus now assures that a full penile tumesence can be achieved at any time.

What I claim is:

1. A surgical appliance for stimulating an erection of the male genital organ comprising:
   an elongated shaped surgical appliance having a vacuum housing portion connected to a pump housing portion and adapted to be held and operated with one hand,
   said vacuum housing having an open end adapted to receive the male genital organ, and a closed end connected to said pump housing,
   a vacuum plenum connected to said closed end of said vacuum housing, in said pump housing
   vacuum pump means in said pump housing connected to said vacuum plenum and having a flexible diaphragm for providing a high vacuum in said vacuum plenum,
   spring means for biasing said flexible diaphragm toward said vacuum housing,
   valve means between said vacuum housing and said vacuum plenum for transferring said high vacuum to said vacuum housing, and
   lever means extending along a side wall of said vacuum housing and connected to said vacuum pump means, whereby each successive operation of said lever means is effective to create a greater vacuum in said vacuum plenum to provide a high vacuum in said vacuum housing.

2. A surgical appliance as set forth in claim 1 wherein said flexible diaphram comprises a flexible washer.

3. A surgical appliance as set forth in claim 2 wherein said flexible washer is provided with a central aperture, and said valve means comprises an exhaust check valve connected through said central aperture to said vacuum plenum.

4. A surgical appliance as set forth in claim 1 wherein said vacuum pump means comprises link means connecting said flexible diaphram to said lever means.

5. A surgical appliance as set forth in claim 1 wherein said vacuum pump means comprises a piston rod having an O-ring seal cooperating with a sleeve mounted in said pump housing.

6. A surgical appliance as set forth in claim 5 wherein said piston rod is connected by a pivot pin to lever means.

7. A surgical appliance as set forth in claim 5 wherein said valve means comprises an exhaust check valve in said piston rod.

8. Erection stimulating apparatus comprising:
   a housing having:
      (a) an open-ended vacuum chamber adapted to receive a flaccid penis and to contain said penis after erection, and
      (b) a pump chamber containing a plenum chamber separated from said vacuum chamber by a partition wall;
   a piston mounted in said pump chamber and extending through an opening into said plenum chamber for reciprocating movement out from and into said plenum chamber, said piston and said opening through which said piston extends into said plenum chamber sized to form a space between said piston and the wall defining said opening;
   a flexible diaphragm attached between said housing and said piston to seal said opening;
   means for moving said piston to:
      (a) draw said piston out from said plenum chamber and reduce the air pressure in said plenum chamber to below atmospheric pressure, and
      (b) move said piston into said plenum chamber and increase the air pressure in said plenum chamber to above atmospheric pressure;
   first valve means in said partition wall and:
      (a) responsive to movement of said piston out from said plenum chamber for placing said vacuum chamber and said plenum chamber in fluid communication when the air pressure in said vacuum chamber exceeds the air pressure in said plenum chamber to reduce the air pressure in said vacuum chamber, and
      (b) responsive to movement of said piston into said plenum chamber for preventing air flow between said vacuum chamber and said plenum chamber when the air pressure in said plenum chamber exceeds the air pressure in said vacuum chamber;
   and second valve means:
      (a) responsive to movement of said piston out from said plenum chamber for preventing air flow between said plenum chamber and the space outside said plenum chamber when the air pressure in said plenum chamber is below atmospheric pressure, and (b) responsive to movement of said piston into said plenum chamber for placing said plenum chamber and said space outside plenum chamber in fluid communication when the air pressure in said plenum chamber is above atmospheric pressure to reduce the air pressure in said plenum chamber to atmospheric pressure.

9. Erection stimulating apparatus according to claim 8 wherein said reciprocating movement of said piston is away from said partition wall to reduce the air pressure in said plenum chamber to below atmospheric pressure and toward said partition wall to increase the air pressure in said plenum chamber to above atmospheric pressure.

10. Erection stimulating apparatus according to claim 8 wherein said flexible diaphragm is folded within said space between said piston and said wall defining said opening through which said piston extends.

11. Erection stimulating apparatus according to claim 10 wherein:
(a) said piston has an air flow passage opening at a first end into said plenum chamber and opening at a second end into said space outside said plenum chamber, and
(b) said second valve means are in said air flow passage in said piston.

12. Erection stimulating apparatus according to claim 10 wherein said moving means includes:
(a) spring means for urging said piston toward said partition wall, and
(b) a lever mounted on said housing and coupled to said piston for moving said piston away from said partition wall against said spring means.

13. Erection stimulating apparatus comprising:
a vacuum chamber housing adapted to receive a flaccid penis and to contain said penis after erection;
a pump chamber housing containing a plenum chamber;
pump means mounted in said pump chamber housing and extending through an opening into said plenum chamber for reducing the air pressure in said plenum chamber to below the air pressure in said vacuum chamber;
a flexible diaphragm attached between said pump chamber housing and said pump means for sealing said opening through which said pump means extend into said plenum chamber;
valve means for alternately placing said plenum chamber in fluid communication with:
(a) said vacuum chamber to move air from said vacuum chamber to said plenum chamber and reduce the air pressure in said vacuum chamber, and
(b) the space outside said plenum chamber to release air in said plenum chamber to said space outside said plenum chamber;
and means mounted in said pump chamber housing for actuating said pump means.

14. Erection stimulating apparatus according to claim 13 wherein said pump means reciprocate and said valve means are responsive to the reciprocating movement of said pump means to place said plenum chamber in fluid communication with:
(a) said vacuum chamber when said pump means move in a first direction to reduce the air pressure in said plenum chamber to below the air pressure in said vacuum chamber, and
(b) said space outside said plenum chamber when said pump means move in a second direction opposite to said first direction.

15. Erection stimulating apparatus according to claim 13 wherein said vacuum chamber housing and said pump chamber housing are both cylindrical and attached to one another end-to-end and said actuating means are mounted in the side wall of said pump chamber housing at a position where said actuating means can be engaged by the same hand of a user of said apparatus as is used to hold said apparatus.

16. Erection stimulating apparatus according to claim 14 wherein said actuating means include a lever coupled to said pump means for moving said pump means in said first direction and said pump means include a spring for urging said pump means to move in said second direction.

17. Erection stimulating apparatus according to claim 16 wherein said vacuum chamber housing and said pump chamber housing are both cylindrical and attached to one another end-to-end and said lever is mounted in the side wall of said pump chamber housing at a position where said lever can be engaged by the same hand of a user of said apparatus as is used to hold said apparatus.

* * * * *